(12) United States Patent
Chevallier et al.

(10) Patent No.: US 8,118,787 B2
(45) Date of Patent: Feb. 21, 2012

(54) SAFETY DEVICE FOR A SYRINGE

(75) Inventors: Stephane Chevallier, Saint-Soupplets (FR); Jean-Michel Chevallier, Enghien-les-Bains (FR)

(73) Assignee: Tech Group Europe Ltd., Osny (FR)

( * ) Notice: Subject to any disclaimer, the term of this patent is extended or adjusted under 35 U.S.C. 154(b) by 0 days.

(21) Appl. No.: 12/738,422

(22) PCT Filed: Oct. 22, 2008

(86) PCT No.: PCT/FR2008/051907
§ 371 (c)(1),
(2), (4) Date: Apr. 16, 2010

(87) PCT Pub. No.: WO2009/056734
PCT Pub. Date: May 7, 2009

(65) Prior Publication Data
US 2010/0211017 A1    Aug. 19, 2010

(30) Foreign Application Priority Data

Oct. 23, 2007  (FR) ...................................... 07 58495

(51) Int. Cl.
*A61M 5/32* (2006.01)
(52) U.S. Cl. .......................... 604/198; 604/192; 604/110
(58) Field of Classification Search .................. 604/110, 604/198, 192, 193, 194, 195, 196, 197, 187
See application file for complete search history.

(56) References Cited

U.S. PATENT DOCUMENTS

| | | | |
|---|---|---|---|
| 6,585,702 B1 * | 7/2003 | Brunel | ........................... 604/263 |
| 2003/0229314 A1 | 12/2003 | McWethy et al. | |
| 2005/0080383 A1 | 4/2005 | Woehr | |
| 2007/0179441 A1 | 8/2007 | Chevallier | |

FOREIGN PATENT DOCUMENTS

| | | | |
|---|---|---|---|
| FR | 2835753 | * | 2/2002 |
| WO | 9835714 A1 | | 8/1998 |
| WO | 2005039678 A2 | | 5/2005 |

* cited by examiner

*Primary Examiner* — Kevin C Sirmons
*Assistant Examiner* — Laura Schell
(74) *Attorney, Agent, or Firm* — Panitch Schwarze Belisario & Nadel LLP

(57) ABSTRACT

The invention relates to a safety device comprising a supporting sleeve (16) for holding the syringe body (10), a protective sleeve (18), and at least one holding tongue (19, 20) which is rigidly connected to the protection sleeve and can be held by the supporting sleeve (16), in the holding position. The piston comprises a cylindrical skirt (13A) that can end up facing a part of the proximal end (16A) of the supporting sleeve, at the end of the injection stroke, in order to co-operate with an actuating part (19B, 20B) of the holding tongue, and to release same in such a way as to enable a relative sliding of the protection sleeve and the supporting sleeve in order to protect the neddle. This proximal end part (16A) has at least one deflection ramp (30, 32) that can co-operate with the skirt (13A), at the end of the piston stroke, in order to deform the skirt in such a way as to bring part of the skirt of the actuating part (19B, 20B) closer to the holding tongue (19, 20).

9 Claims, 5 Drawing Sheets

SAFETY DEVICE FOR A SYRINGE

CROSS-REFERENCE TO RELATED APPLICATIONS

This application is a Section 371 of International Application No. PCT/FR2008/051907, filed Oct. 22, 2008, which was published in the French language on May 7, 2009 under International Publication No. WO 2009/056734 A2 and the disclosure of which is incorporated herein by reference.

BACKGROUND OF THE INVENTION

The present invention relates to a safety device for a syringe which has a syringe body, a plunger assembly and a needle, where the device includes a support sleeve suitable for retaining the body of the syringe relative thereto, a protection sleeve and at least one retaining tab rigidly connected to the protection sleeve and suitable for occupying a retained position in which the tab is retained relative to the support sleeve and a released position in which said tab stops being retained relative to the support sleeve to allow relative sliding of the protection sleeve and the support sleeve towards a protection position in which the needle is surrounded by the protection sleeve, where the plunger assembly has a cylindrical skirt suitable, at the end of the injection stroke of said plunger assembly, for coming opposite a proximal end portion of the support sleeve for engaging with an actuating part of the retaining tab for urging said tab towards the released position thereof.

In the meaning of the invention, the proximal end of an element is the one which is the closest the fingers of the user giving an injection by using the device, whereas the distal end is the opposite end.

A device of this type is known from documents EP-A 1,235,603 and EP-A 1,474,194.

In EP 1,235,603, the cylindrical skirt of the plunger assembly is thick, such that it is rigid, and has a frustruconical internal shape allowing it to come into contact with the inclined external surfaces of the two retention tabs, to bring these tabs back towards the inside, meaning towards the vertical axis of the device, so as to free them from being retained relative to the support sleeve. For the release of the tabs to occur reliably and systematically, it is necessary for the skirt to be thick and rigid and that the tabs be accessible for this skirt. Thus, the tabs are relatively remote from the central axis of the device because they are located on either side of the collar of the syringe body which serves to retain this body relative to the support sleeve.

With a device of the type described in EP 1,235,603, it is therefore necessary to use a plunger assembly which has a skirt with a particular confirmation and a large radial dimension.

In EP 1,474,194, the skirt has the shape of a portion of a cylinder whose lower end is slightly chamfered on the inner side. This time, the tabs for retaining the protection sleeve relative to the support sleeve are substantially contained in the bulk of the collar of the syringe body when they are in their retained position. Consequently, these tabs are not easily accessible for the skirt of the plunger assembly, such that relay tabs, rigidly connected with the support sleeve, are necessary. At the end of the injection, the skirt comes to bringing the relay tabs back to the inside, and these tabs engage with the tabs for retention of the protection sleeve in order to also return these latter to the inside.

In sum, the bulk of the device in the radial direction is relatively large.

BRIEF SUMMARY OF THE INVENTION

The purpose of the present invention is to further improve the state of the aforementioned art, by making it possible to manufacture the skirt of the plunger assembly for lower-cost and assure the safe release of the one or more retaining tabs by this skirt at the end of the injection, while also allowing the radial dimensions of the device to be as small as possible.

This purpose is achieved because of the fact that the proximal end portion of the support sleeve has at least one deflection ramp suitable, at the end of the plunger assembly stroke, of engaging with said skirt for deforming the skirt so as to bring a portion of said skirt closer to the actuating part of the retention tab to enhance the engagement between the skirt and the actuating part.

The skirt can have the shape of a portion of cylindrical wall, which is slightly radially deformable by pressure. At the end of the injection stroke, the deflection ramp deforms the skirt in order to assure a reliable contact between the skirt and the actuating part of the retention tab. In contrast to what is shown in EP 1,474,194, the skirt thus directly contacts the one or more retention tabs. However, this contact results reliably from the presence of the deflection ramp. Thus, even if the one or more retention tabs are at least in part contained in the radial bulk of a collar that the syringe body could have, the one or more tabs can be brought back into their released position by the skirt.

In contrast to EP 1,235,603, the skirt can have reduced radial dimensions so as to allow the actuation of the device, meaning the relative movement of the protection sleeve and the support sleeve, without the one or more retention tabs extending a large distance from the axis of the device, nor in particular around a collar that the syringe body could have.

Advantageously, at least in the retained position of the retention tab, the actuating part of this retention tab is arranged substantially opposite from the deflection ramp.

This position makes it possible to assure that the deformation of the skirt of the plunger assembly needed for the release of the retention tab is achieved in the right area.

Advantageously, the proximal end part of the support sleeve forms a cylindrical cavity into which the cylindrical skirt of the plunger assembly is suited for entering at the end of the injection stroke thereof, and the ramp is formed on at least one annular rib portion arranged on the internal axial wall of said cavity.

This constitutes a simple means for implementing the deflection ramp.

Advantageously, the actuating part of the retention tab is formed on an outer side of the retention tab, and the deflection ramp is formed on the inner periphery of the support sleeve.

Advantageously, the syringe body has a collar located at the proximal end of this body and, at least in its retained position, the retention tab extends between this collar and the distal end of the syringe body, and this retention tab is at least in part located in the radial bulk of the collar when this tab is urged by the cylindrical skirt towards its released position.

In fact, despite the fact that this tab is at least partially "masked" by the bulk of the collar, it is accessible for the skirt because of the deformation thereof achieved by the deflection ramp. This makes it possible to considerably reduce the radial dimensions of the device.

According to an advantageous arrangement, the protection sleeve is fitted into the support sleeve, and the retention tab is rigidly connected with the protection sleeve and has, on the outer periphery thereof, a retention projection enabling the retention thereof relative to a retention rib which the support sleeve has.

According to another advantageous arrangement, the support sleeve is fitted into the protection sleeve, the proximal end part of the support sleeve has a portion of the outer axial wall on which the ramp is formed, and the actuation part of the retention tab is formed on an outer edge of the retention tab.

The invention will be better understood and its advantages more apparent upon reading the detailed description which follows of the embodiments shown as examples without limitation.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The description refers to the attached drawings, in which in the drawings.

DETAILED DESCRIPTION OF THE INVENTION

Figure 1:
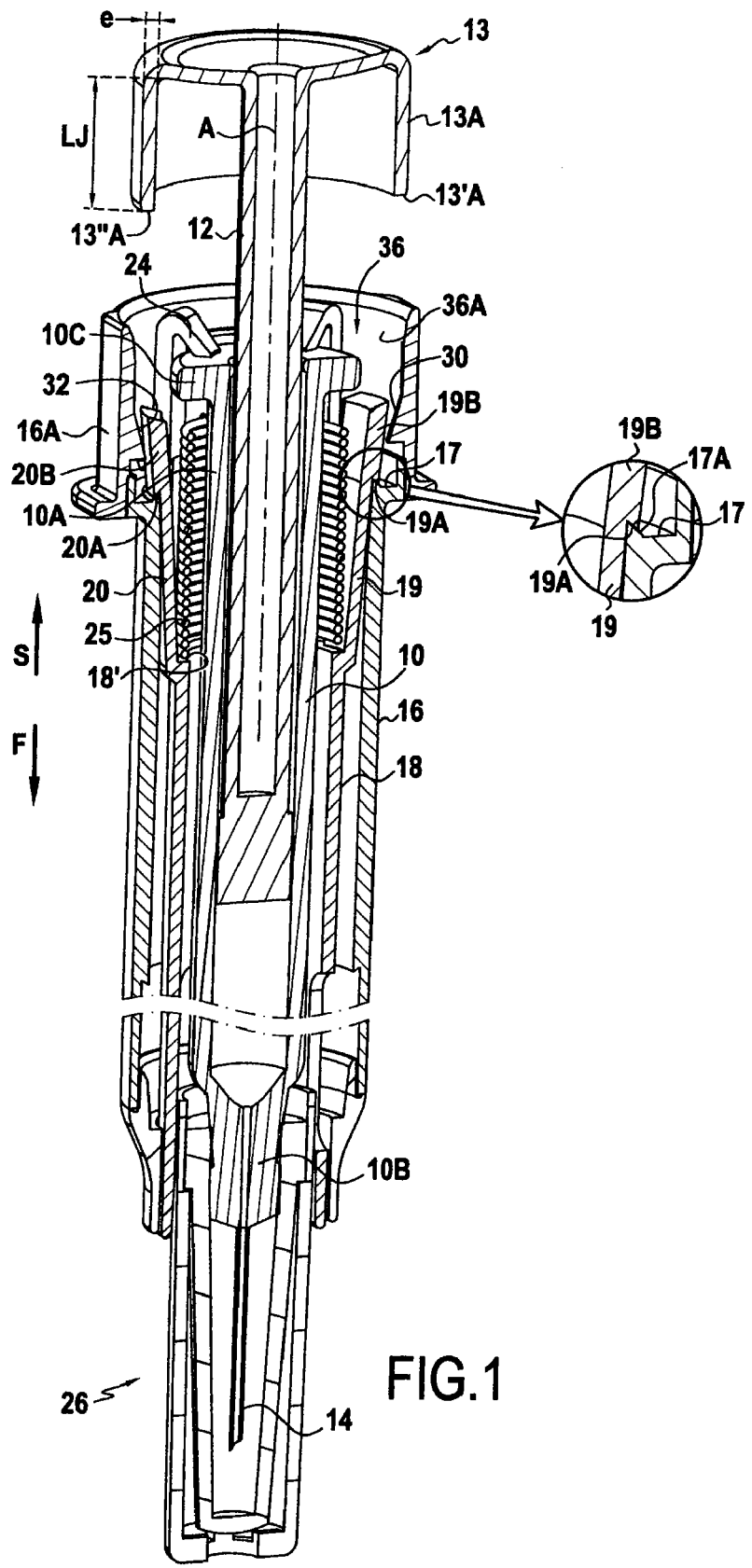
FIG. 1 is a is a perspective, cross-sectional view in an axial plane of a device conforming to the invention according to a first embodiment.
Figure 2:
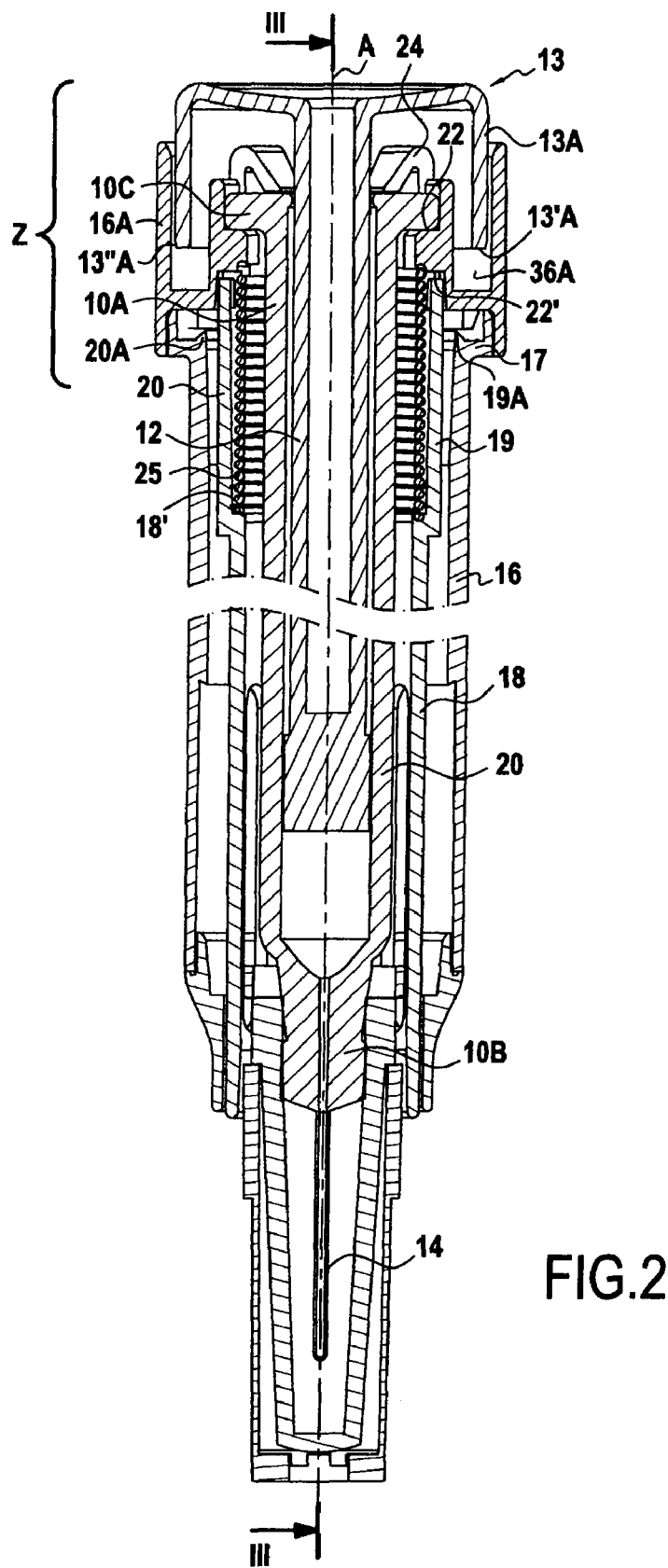
FIG. 2 is a is an axial sectional view of the device, taken perpendicularly to the section of FIG. 1, when the plunger assembly comes to the end of the injection.
Figure 3:
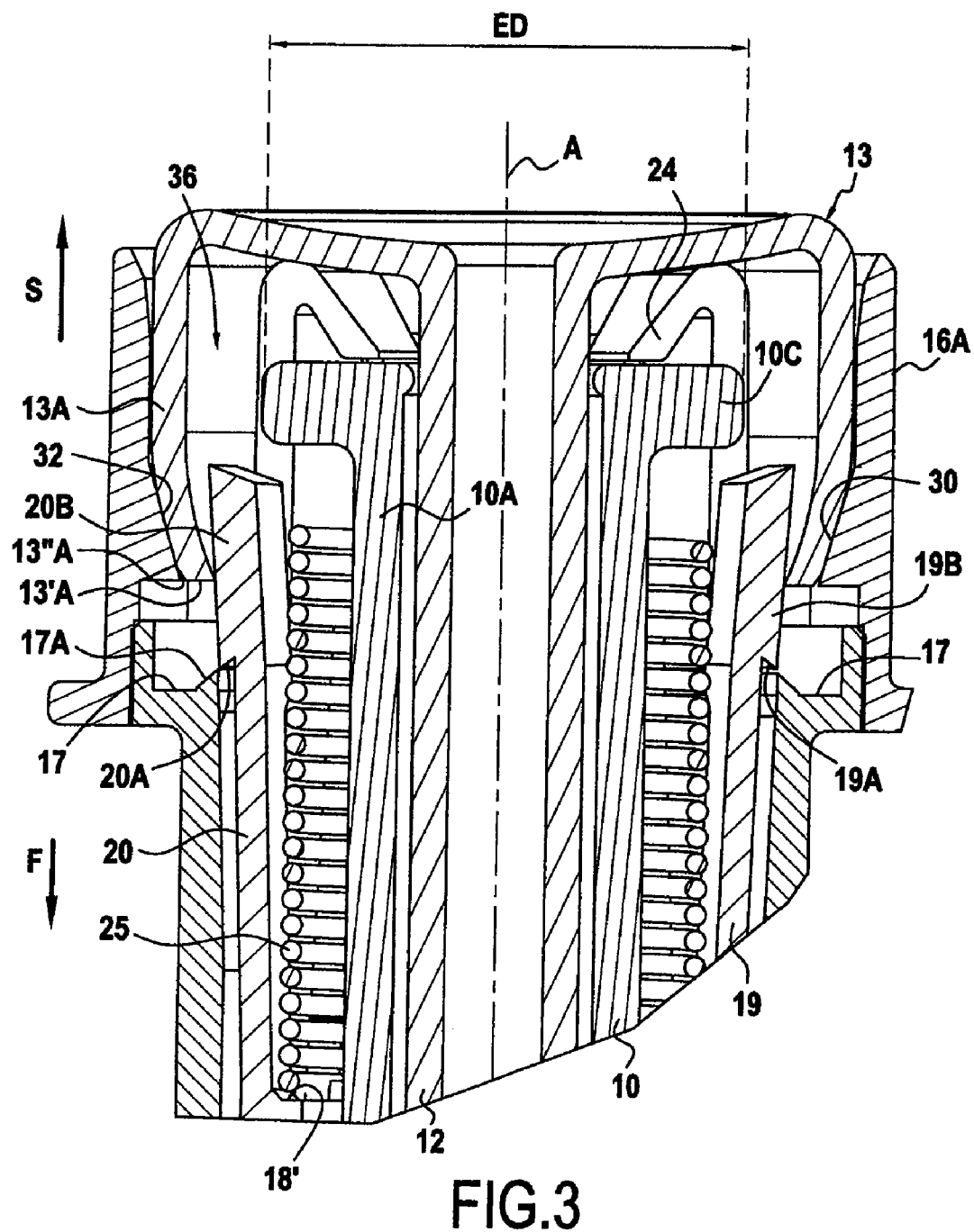
FIG. 3 is a is an enlarged view of the zone Z from FIG. 2, taken along a section in the plane corresponding to that of the section from FIG. 1.
Figure 4:
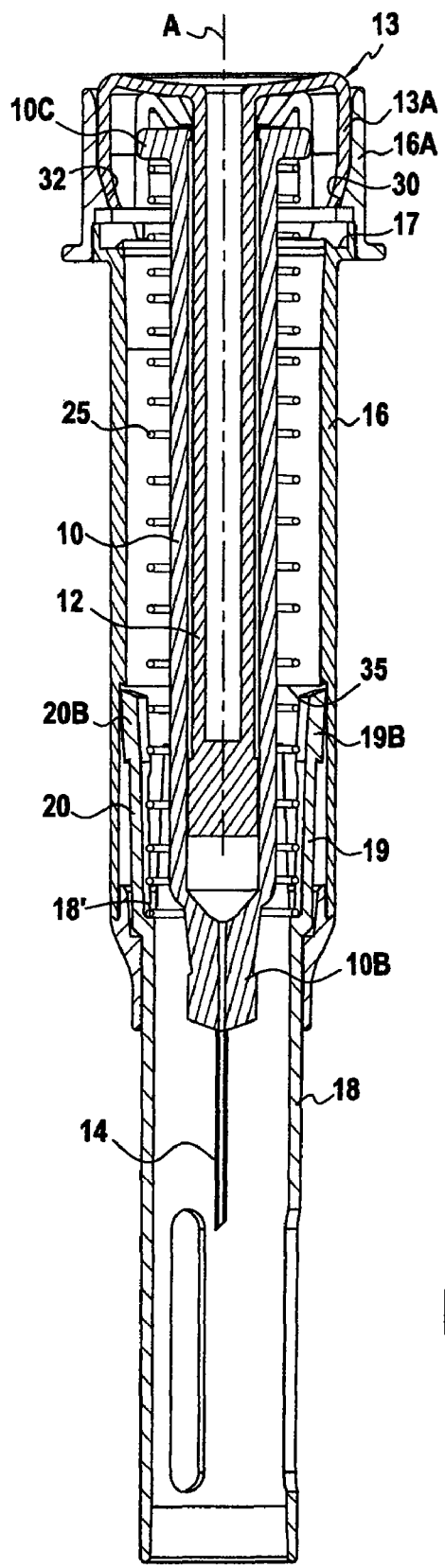
FIG. 4 is a is a view in the same section as FIG. 3, showing the device after the injection, while the needle is protected by the protection sleeve.

The device shown in FIGS. 1 to 4 includes a syringe having a syringe body 10, a plunger assembly 12 which can slide in the body, from a proximal end 10A thereof, between a ready position in which it is shown in FIG. 1 and an after injection position in which it is shown in FIG. 4. Opposite the plunger assembly, meaning at the distal end 10B of the syringe body, a needle 14 is connected to the body. The syringe body is preferably glass or plastic.

The safety support device for the syringe includes, according to the first embodiment, a support sleeve 16 and a protection sleeve 18 which is fitted into the support sleeve 16 and arranged to be able to slide relative to the support. In the ready position before the injection, the protection sleeve 18 is retained inside the support sleeve 16 by two retaining tabs, respectively 19 and 20, which are rigidly connected to the protection sleeve 18 and are retained relative to the support sleeve 16. In fact, these tabs are positioned to be able to latch onto a shoulder 17 which the support sleeve has in the area of its proximal end 16A. For this purpose the tabs have a projection, respectively 19A and 20A, which latch onto the rim of the shoulder 17. As can be seen better in FIG. 1, the rim 17A projects slightly in the direction S, going from the distal end towards the proximal end, so as to form a retention rib.

The projections from the tabs and the rim have the shape of ramps inclined upwards to make the latching and unlatching of the retention tabs easier.

For its part, the syringe body is retained relative to the support sleeve by the collar 10C thereof, which rests in part on a shoulder 22 of the support sleeve so as to block the movement of the syringe body relative to this sleeve in the injection direction F opposite the direction S, where the collar is additionally retained against displacement in the direction S by elastic holding tabs 24 which are rigidly connected with the support sleeve 16. A spring 25 is placed between a first support surface fixed relative to the support sleeve formed by the lower surface 22' of the shoulder 22 and a second support surface fixed relative to the projection sleeve formed by a lower shoulder 18' of the sleeve. At the distal end thereof, the syringe body has a cap 26, which covers the needle 14, and which can be removed in order to expose this needle so as to allow an injection.

Once the assembly constituted of the support sleeve 16, protection sleeve 18 and spring 25 is assembled, the syringe body bearing the cap 26 can be placed inside the protection sleeve by the proximal end thereof, until the collar comes to a stop against the shoulder 22 and is retained by the tabs 24 which flex by elastic flexion upon passing this collar.

For more details, refer to the document EP 1,474,194 which shows a device whose configuration is substantially analogous to that of the device from the invention, for what was just described.

It can be seen in FIGS. 1, 3 and 4 that the support sleeve 16 has, in its proximal end portion, two flexion ramps, respectively 30 and 32, which—when the protection sleeve 18 is in the retracted position thereof inside the support sleeve 16, meaning when the retention tabs 19 and 20 are in their retained position—is arranged opposite from the actuating parts of these tabs constituted of the heads thereof adjoining the free ends thereof, respectively 19B and 20B.

The head 13 of the plunger assembly has a cylindrical skirt 13A which, as can be seen in FIG. 3, comes in contact with the actuating portions 19B and 20B of retaining tabs 19 and 20 to bring them towards the central longitudinal axis A of the device and thereby cause the release of the projections 19A and 20A from the shoulder 17. In other terms, the engagement between the skirt and the actuating portions of the tabs unhooks these tabs and thereby allows the automatic forward movement of the protection sleeve in the direction F, towards the distal end, so that the sleeve comes around the needle 14 and thus protects it.

The ramps 30 and 32, and the actuating portions 19B and 20B of the tabs 19 and 20 overlap axially. Consequently, when the lower end 13'A (meaning the distal end) of the skirt 13A comes in contact with the ramps 30 and 32, this skirt is locally deformed so as to come closer to the axis A, meaning in order to bring the deformed portion in contact with the ramps closer to the actuating parts of the retaining tabs, and thereby help the engagement between the skirt and these actuating tabs. In other words, the free edges of the skirt in contact with the ramps are curved inward towards the axis A to help the unhooking of the tabs 19 and 20.

As in the example shown, it is advantageous for the inflection ramps to form one or more discontinuous portions of an annular rib. In fact, the discontinuities in this rib form spaces aiding the deformation of the skirt. Thus, if two diametrically opposite ramps are provided, they have a tendency to make the edge 13'A of the skirt oval which, in the ramp regions, will define smaller radial dimensions than those that the skirt will have in the discontinuities of the aforementioned rib. Thus, the skirt has a lower resistance to the deformation, and the pushing of the plunger assembly in the injection direction remains easy.

The plunger assembly can be made in a single part of a plastic material of the type commonly used for making syringe plunger assemblies. For example it could be polyolefin or an analog. The thickness of the skirt is chosen so that it has both mechanical integrity and is also easily deformable. In particular, this thickness e will be chosen of about 0.5 to 1.5 mm, preferably of about 1 mm, whereas the length LJ of the skirt is of about 1 cm.

It can be seen in the figures that the proximal end part 16A of the support sleeve 16 forms a cylindrical cavity 36 into which the cylindrical skirt 13A is able to enter after the injection stroke of the plunger assembly. The inflection ramp (s) are formed on an annular rib portion arranged on the internal axial wall 36A of this cavity. Further, for the retention tab(s), the actuating part 19B, 20B is formed on an outer side of the tab (meaning on the side farther from the axis A) whereas the deflection ramps 30, 32 are formed on the inner periphery of the element bearing them, in this case the support sleeve 16.

FIG. 3 shows the situation when the end 13'A of the skirt 13A engages with the actuating parts 19B, 20B of the retaining tabs 19, 20, just before these tabs are unhooked from the shoulders 17. It can therefore be seen that these tabs are in part contained in the radial bulk ED of the collar 10C. In other words, when they are urged towards their released position, the tabs in part are housed under the collar 10C, meaning between the collar and the distal end of the syringe body. Despite this, the tabs remain accessible for being urged by the skirt 13A because of the presence of the ramps 30, 32. Thus the overall radial bulk of the device can be minimized.

It is shown that the free end 13'A of the skirt 13A has a chamfer 13"A on its outer side. This chamfer aids the sliding of this free end on the ramps 30 and 32 reducing any blockage during the pushing of the plunger assembly.

FIG. 4 shows the device once the retaining tabs 19 and 20 have been unhooked from the shoulders 17, thereby allowing the protection sleeve 18 to exit under the effect of the restoring force exerted by the spring 25. Then it can be seen that the return of the protection sleeve 18 inside the support sleeve 16 is blocked by the engagement of the free ends of the tabs 19 and 20 and a shoulder 35 in the inner wall of the support sleeve, turned towards the distal end.

Figure 5:
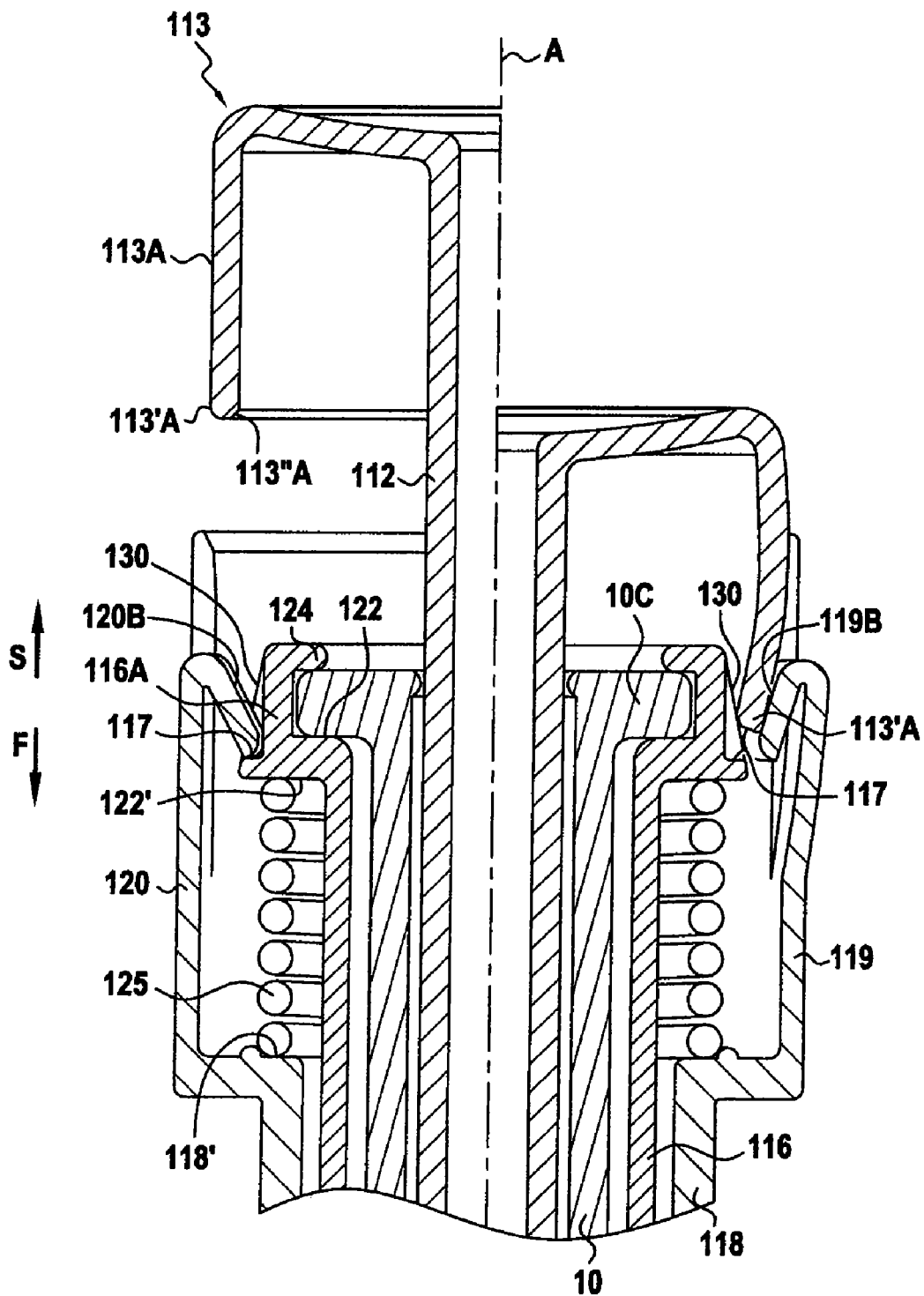
FIG. 5 is a is a partial axial sectional view of the device conforming to the invention, according to another embodiment, showing two positions of the device.

Now the second embodiment from FIG. 5 will be described. On the left half of this figure, the device is shown while injecting, while the retaining tabs are in the retained position, whereas in the right half, the retention tabs are being released.

In this embodiment, the support sleeve 116 is arranged inside of the protection sleeve 118. The syringe body is retained relative to the support sleeve because of the fact that the collar 10C of this body is retained between a shoulder 122 turned towards the proximal end and a latching rib or analogue 124 spaced from the shoulder. The shoulder and the rib are rigidly connected to the sleeve 116 and, more specifically, are located at the proximal end 116A thereof. The restoring spring 125 is arranged between the supporting surface 122' which is fixed relative to the sleeve 116 and is made up by the opposite surface of the shoulder 122, and the supporting surface 118' which is fixed relative to the protection sleeve 118 and is turned towards the proximal end. Retention tabs 119, 120 which are rigidly connected with the protection sleeve 118 serve to retain the protection sleeve relative to the support sleeve.

More precisely, as can be seen in the left half of the figure, the retaining tab 120 is resting on a shoulder 117 of the support sleeve 116 which is turned towards the proximal end. In this case, this engagement is done by the free end of the tab which is shaped as a hook which is directed towards the distal end. Thus, the tab hooks on the shoulder 117 and blocks the movement of the support sheath in the direction S opposite the injection direction F. As can be better seen in the right part of the figure, the shoulder 117 is adjacent to a deflection ramp 130 which is arranged on the outside axial periphery of the support sleeve 116. In this case, two ramp portion are arranged on either side of the shoulder 117 which is thereby formed by the radial surface of a projection formed between the two ramp portions.

On the right part of the figure it is seen that, after injection, the skirt 113A of the plunger assembly 120 engages with actuating part 119B of the tab 119 to flex the tab towards the outside, in the direction away from the axis A, so as to unhook the tab from the shoulder 117. It is obviously the same for the actuating part 120B of tab 120. Thus, support sleeve 116 and the syringe body 10 that it carries can be moved relative to the protection sleeve 118 in the direction S opposite the injection direction F, until the needle is returned inside the distal end (not shown) of the protection sleeve 118

Advantageously, the tabs 119 and 120 are formed from cutouts of the cylindrical wall of the protection sleeve 118. In this embodiment as well, the ramps 130 help the deformation of the skirt 113A for securing its engagement with the actuating parts 119B and 120 of the tabs 119 and 120 and thereby reliably unhooking them. The free end 113'A of the skirt 113A has, on its inner surface, a chamfer 113"A aiding the sliding of this free end on the ramps. Again this time, the skirt 113A is made oval through contact thereof with the ramps, but the radial dimensions thereof increase locally in the zones of contact with the ramps, whereas they get smaller in a section transverse to the one which is shown.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A safety device for a syringe having a syringe body (10), a plunger assembly (12; 112) and a needle (14), where the device includes a support sleeve (16; 116) suitable for retaining the body of the syringe (10) relative thereto, a protection sleeve (18; 118) and at least one retention tab (19, 20; 119, 120) rigidly connected to the protection sleeve and suitable for movement between a retained position in which this tab is retained relative to the support sleeve and a released position in which said tab stops being retained relative to the support sleeve to allow relative sliding of the protection sleeve and the support sleeve towards a protection position in which the needle (14) is surrounded by the protection sleeve (18; 118), where the plunger assembly has a cylindrical skirt (13A; 113A) suitable, at the end of the injection stroke of said plunger assembly, for engaging with an actuating part (19B, 20B; 119B, 120B) of the retaining tab for urging said tab towards the released position thereof, wherein a proximal end portion (16A; 116A) of a support sleeve (16; 116) has at least one deflection ramp (30, 32; 130) suitable, at the end of the injection stroke, for engaging with said skirt (13A; 113A) for deforming the skirt to bring a portion of said skirt closer to the actuating part (19B, 20B; 119B, 120B) of the retention tab (19, 20; 119, 120) to enhance the engagement between the skirt and the actuating part.

2. The safety device according to claim 1, wherein at least in the retained position of the retention tab (19, 20), the actuating part (19B, 20B) of this retention tab is arranged radially inwardly from the deflection ramp (30, 32).

3. The safety device according to claim 1, wherein the proximal end portion (16A) of the support sleeve (16) forms a cylindrical cavity (36) into which the cylindrical skirt (13A) of the plunger assembly (12) is suited for entering at the end of the injection stroke thereof, and the ramp (30, 32) is formed on at least one annular rib portion arranged on the internal axial wall of said cavity.

4. The safety device according to claim 1, wherein the actuating part (19B, 20B) of the retention tab (19, 20) is formed on an radially outward side of the retention tab, and the deflection ramp (30, 32) is formed on the inner periphery of the support sleeve (16).

5. The safety device according to claim 4, wherein the syringe body (10) has a collar (10C) located at a proximal end (10A) of the body, and, with the tab in the released position, the retention tab (19, 20) is at least in part located radially inwardly of the outermost radial extent of the collar (10C).

6. The safety device according to claim 1, wherein the retention tab (19, 20) has, on an outer periphery thereof, a retention projection (19A, 20A) enabling retention of the protection sleeve relative to a retention rib (17A) of the support sleeve (16).

7. The safety device according to claim 1, wherein the support sleeve (116) is fitted into the protection sleeve (118); the proximal end part (116A) of the support sleeve has a radially outward axial wall on which the ramp (130) is formed; and the actuation part (119B) of the retention tab (119, 120) is formed on a radially inward portion of the retention tab.

8. The safety device according to claim 1, further comprising a spring (25, 125) arranged between a first supporting surface (22'; 122') fixed relative to the support sleeve (16, 116) and a second supporting surface (18', 118') fixed relative to the protection sleeve (18, 118) for urging the relative sliding of these sleeves.

9. A safety device for a syringe having a needle comprising:
a syringe body;
a support sleeve for retaining the syringe body, the support sleeve having a proximal end portion that includes at least one deflection ramp;
a protection sleeve having at least one retention tab rigidly connected to the protection sleeve and movable between a retained position in which the retention tab is retained relative to the support sleeve and a released position in which the retention tab releases from the support sleeve to allow the protection sleeve to slide relative to the support sleeve towards a protection position in which the needle is surrounded by the protection sleeve; and
a plunger assembly movable within the syringe body, the plunger assembly having a cylindrical skirt that engages the deflection ramp at an end of an injection stroke and bends radially inwardly to urge the retention tab towards the released position.

* * * * *